United States Patent [19]

Solomon et al.

[11] Patent Number: 4,521,564

[45] Date of Patent: Jun. 4, 1985

[54] COVALENT BONDED ANTITHROMBOGENIC POLYURETHANE MATERIAL

[75] Inventors: Donald D. Solomon, Spring Valley; Charles W. McGary, Centerville; Vincent J. Pascarella, Dayton, all of Ohio

[73] Assignee: Warner-Lambert Company, Morris Plains, N.J.

[21] Appl. No.: 578,909

[22] Filed: Feb. 10, 1984

[51] Int. Cl.³ .................... C08H 1/00; A61F 1/00; C08B 37/10

[52] U.S. Cl. .................. 525/54.1; 523/112; 525/54.2; 525/54.22; 525/123; 525/127; 525/131; 525/452

[58] Field of Search ............ 523/112; 525/54.1, 54.2, 525/54.22, 127, 131, 123, 452

[56] References Cited

U.S. PATENT DOCUMENTS

| | | | |
|---|---|---|---|
| 3,616,935 | 11/1971 | Love et al. | 210/500 |
| 3,617,344 | 11/1971 | Leininger et al. | 117/47 |
| 3,826,678 | 7/1974 | Hoffman et al. | 117/81 |
| 3,846,353 | 11/1974 | Grotta | 523/112 |
| 3,853,804 | 12/1974 | Yen | 260/32.6 |
| 4,046,725 | 9/1977 | Pusineri | 269/9 |
| 4,098,645 | 7/1978 | Hartdegen | 525/54.1 |
| 4,195,127 | 3/1980 | Hartdegen | 525/54.1 |
| 4,243,776 | 1/1981 | Marconi | 523/112 |
| 4,273,873 | 6/1981 | Sugitachi | 435/180 |
| 4,326,532 | 4/1982 | Hammar | 128/349 |
| 4,378,803 | 4/1983 | Takagi | 523/112 |
| 4,415,490 | 11/1983 | Joh | 525/54.2 |

OTHER PUBLICATIONS

Larm et al., "New Non. Thrombogenic Surface Prepared by Selective Covalent Binding of Heparin . . .", Biomat., Med. Dev., Art., Org., 11, (283), pp. 161–173, (1983).

Salyer et al., "New Blood-Compatible Polymers for Artificial Heart Application", J. Biomed. Mater. Res. Symposium, vol. 1, pp. 105–127, (1971).

*Primary Examiner*—C. Warren Ivy
*Attorney, Agent, or Firm*—Gary M. Nath

[57] ABSTRACT

Antithrombogenic polyurethane polymers having the antithrombogenic material covalently bound to the polyurethane.

23 Claims, No Drawings

COVALENT BONDED ANTITHROMBOGENIC POLYURETHANE MATERIAL

The present invention relates to a novel antithrombogenic polyurethane polymer and process for making the same. More particularly the invention relates to a polyurethane polymer having an antithrombogenic material covalently bound thereto so that the material is permanently affixed to the polymer and remains virtually nonleachable when the products made from the reaction product are in use.

Extensive investigations have been undertaken over many years to find materials that will be biologically and chemically stable towards body fluids. This area of research has become increasingly important with the development of various objects and articles which can be in contact with blood, such as artifical organs, vascular grafts, probes, cannulas, catheters and the like.

Artificial materials are being increasingly used as blood contact devices and may be subject to potential generation of thrombus. When blood contacts a foreign material, a complex series of events occur. These involve protein deposition, cellular adhesion and aggregation, and activation of blood coagulation schemes. Considerable research effort has been focused on this blood-material-interaction in the last twenty years. The overall objective of these investigations has been to minimize the potential for thrombus formation on the foreign materials, such as the device when introduced into the body upon contact with blood.

Early work by R. I. Leininger and R. D. Falb, U.S. Pat. No. 3,617,344, was based on binding quaternary amines to a polymer surface and subsequently ionically binding heparin thereto. In contrast, H. M. Grotta established a method in U.S. Pat. No. 3,846,353 in which heparin was complexed with a quaternary amine on a polymer surface. Both the Leininger and Grotta methods have the disadvantage of being non-permanent or leachable systems. In general, ionically bound systems have limited viability due to their inherent leachability. J. Love and G. W. Holmes patented a method for the preparation of antithrombogenic surfaces in U.S. Pat. No. 3,616,935 wherein polyalkylenimines are used to irreversibly adsorb the antithrombogenic compound to cellulose, cellulose esters, silicone rubber, polypropylene, polycarbonate and glass through the formation of ionic bonds. The Love et al. technique, however, was not able to overcome the deficiencies of the prior techniques, notably leaching of the antithrombogenic material rendering the system non-permanent and ineffective for long term internal use in the body.

U.S. Pat. No. 3,826,678 of A. S. Hoffman and G. Schmer relates to a covalent bonding method involving the use of "soft" hydrogel surfaces wherein radiation grafting is employed with a reactable compound selected from polymers and copolymers on an inert polymeric substrate and thereafter a biologically active compound is chemically bound to the reactable compound. "Soft" gel-like surfaces are not appropriate for devices such as catheters or other medical devices which require a "hard" polymer surface. The "soft" hydrogel or hydrophilic surface of the Hoffman et al. patent would be subject to being stripped off catheters and in case of other blood contact devices, be devoid of the mechanical properties required. "Hard" polymers would provide the mechanical strength required in such applications.

In contrast to the aforementioned techniques, U.S. Pat. No. 4,326,532 to Hammar discloses a layered medical article having an antithrombogenic surface wherein a natural or synthetic polymeric substrate is reacted with chitosan and the antithrombogenic is then bonded to the chitosan. Hammar disclosed on column 3, lines 10 to 49 that the antithrombogenic material may be ionically bonded to the chitosan or covalently bonded using boron hydrides.

It would be desirable to provide a material which has excellent biological and chemical stability towards body fluids, namely blood, which retains its antithrombogenic agent in a permanent and non-leachable fashion when in contact with blood. It would also be desirable to provide materials which, while being biocompatible, are also biofunctional, that is materials which have biological activity in a variety of functions.

The present invention accomplishes all of these needs by use of a covalently bonded antithrombogenic agent to a solid support. More particularly the invention involves an antithrombogenic polyurethane polymer having: a polyurethane substrate, a polymeric amine selected from the group consisting of a polyvinyl amine, a polyalkylenimine having 2 to 4 carbon atoms per amine unit and mixtures thereof covalently bonded to said polyurethane substrate; and an antithrombogenic agent covalently bonded to said polymeric amine.

In another embodiment, the present invention involves a process for imparting antithrombogenic activity to polyurethane polymer materials which comprises: treating the surface of the polyurethane polymer material with a solution of a polymeric amine selected from the group consisting of a polyvinyl amine, a polyalkylenimine having 2 to 4 carbon atoms per amine unit and mixtures thereof so that the polymeric amine becomes covalently bonded to said polyurethane substrate and wherein the pH of the polymeric amine solution is at least 5.0; washing said surface essentially free of any non-covalently bonded polymeric amine; and treat the surface with an activated antithrombogenic agent to covalently bond the antithrombogenic agent to the polymeric amine.

The term antithrombogenic agent or material as used herein refers to any material which inhibits thrombus formation on its surface, such as by reducing platelet aggregation, dissolving fibrin, enhancing passivating protein deposition, or inhibiting one or more steps within the coagulation cascade. Illustrative antithrombogenic material may be selected from the group consisting of heparin, prostaglandins, urokinase, streptokinase, sulfated polysaccharide, albumin and mixtures thereof. The antithrombogenic material may be used in varying amounts depending on the particular material employed and ultimate desired effect. Preferred amounts have generally been found to be less than about 5% by weight of the final products and may range from about 0.2% to about 5% by weight.

The polyurethane polymers used in the invention as the support structure may be selected from a wide range of thermosetting polyurethane polymers and thermoplastic polyurethane polymers. The particular formations do not constitute a critical aspect of this invention other than to serve as a support substrate for the antithrombogenic agent. The polyurethanes are preferably preformed into the desired shape or structure for the particular application prior to treatment according to the invention. Of significant importance is the ability of the polyurethane polymer to bind the polymeric amine with the antithrombogenic agent in order to effect irreversible coupling. This may be achieved by direct alteration of the polyurethane surface to enable activation of amine and hydroxyl groups from the urethane component. Alternately, various compositions may be chemically bound to the polyurethane surface which contain reactive amine and/or hydroxyl groups.

The chemical modification of the polyurethane surface may be achieved by conventional procedures, such as "etching" the surface with concentrated hydrochloric acid. Concentrated hydrochloric acid results in partial hydrolysis of the polyurethane component rendering free amino and hydroxyl groups which may be subsequently reacted with the polymeric amine directly by exchange condensation. When hydrochloric acid is employed, concentrations of 0.5 normal to 5.0 normal at about 15° C. to 50° C. temperatures for about 5 to 20 hour times have been found quite suitable. It should be recognized that the concentration, time and temperature may vary greatly depending on such factors as type of polyurethane polymer and degree of free amino group desired.

Alternatively, the polyurethane polymer surface may be coupled with a polyurethane prepolymer containing an excess of unreacted NCO units present in the polyisocyanate component. While the number of free NCO units may vary widely, it has been found to preferably employ a polyisocyanate prepolymer containing about 2% to about 30% free NCO units based upon the weight of the prepolymer. Amounts below about 2% have been found to be ineffective in bonding sufficient amounts of polymeric amine whereas amounts greater than 30% result in the formation of polyurethane prepolymers that are difficult to handle.

When a prepolymer is used, the polyurethane surface is contacted with the preblended polyurethane prepolymer having a concentration in solution of about 5% to about 40% (weight to weight). The prepolymers contain conventional polyisocyanates and polyhydric alcohols.

The polyisocyanates useful in the invention in introducing the urethane linkage into the polymer chain may be selected from a wide range of aliphatic, cycloaliphatic and aromatic polyisocyanates. Useable diisocyanates may contain noninterfering groups, e.g., aliphatic hydrocarbon radicals such as lower alkyl or other groups, having substantially nonreactive hydrogens as determined by the Zerewitinoff test, J. Am. Chem. Soc. 49,3181 (1927). The diisocyanate often has at least 6 carbon atoms and usually does not have more than about 40 carbon atoms. Diisocyanates of about 8 to 20 atoms in the hydrocarbon group are preferred. Suitable diisocyanates include 2,4-toluene diisocyanate; 2,6-toluene diisocyanate; 1,4-cyclohexane diisocyante; dicyclohexylmethane 4,4'-diisocyanate; xylene diisocyanate; 1-isocyanate-3-isocyanatomethyl-3,5,5-trimethylcyclohexane; hexamethylene diisocyanate; methylcyclohexyl diisocyanate; 2,4,4-trimethylhexylmethylene diisocyanate, isocyanates such as m-phenylene diisocyanate; mixtures of 2,4- and 2,6 hexamethylene-1,5-diisocyanate; hexahydrotolylene diisocyanate (and isomers), naphtylene-1,5-diisocyanate 1-methoxyphenyl-2,4-diisocyanate, diphenylmethane 4,4'-diisocyanate, 4,4'-biphenylene diisocyanate, 3,3'-dimethoxy- 4,4-biphenyl diisocyanate, 3,3'- dimethyl- 4,4'-biphenyl diisocyanate, and 3,3'-dimethyl-diphenylmethane- 4,4'-diisocyanate and mixtures thereof. The aliphatic and alicyclic diisocyanates employed in the process of this invention and the products made therefrom generally exhibit good resistance to the degradative effects of ultraviolet light.

The polyisocyanate component used to form the prepolymers may contain a portion of polyisocyanates having more than two isocyanate (NCO) groups per molecule providing the urethane polymer compositions are not unduly deleteriously affected. The preferred polyisocyanate is selected from the group consisting of 4,4'-diphenylmethane diisocyanate, toluene diisocyanate, isophorone diisocyanate and methylene bis (4-cyclohexyl) diisocyanate.

The high molecular weight glycols useful in the present invention may be a polyether diol or polyester diol and range in number average molecular weight from about 400 to about 3,000 and preferably about 500 to about 2,000. The low molecular weight glycols may also be used to prepare the prepolymer which materials may have from about 2 to 10 carbon atoms. Exemplary of the polyols which may be employed to prepare polyester polyols are 1,6-hexanediol, neopentyl glycol, trimethylol propane, ethylene glycol, diethylene glycol, triethylene glycol, 1,4-butanediol, 1,4-cyclohexane, 1,2-propanediol, 1,3-propanediol, 1,3-butylene glycol, 1,4-cyclohexane dimethanol, 1,6-hexanediol, and the like, and mixtures thereof. The preferred low molecular weight glycol is 1,4-butanediol. Illustrative polyesters may contain hydroxyl groups, for example, reaction products of polyhydric alcohols reacted with divalent carboxylic acids. It is also possible to use the corresponding polycarboxylic acid anhydrides or corresponding polycarboxylic acid esters of lower alcohols or mixtures thereof, for producing the polyesters. the polycarboxylic acids may be aliphatic, cycloaliphatic, aromatic and/or heterocyclic and may optionally be substituted, for example, by halogen atoms and/or unsaturated. Examples of polycarboxylic acids of this kind include succinic acid, adipic acid, suberic acid, azelaic acid, sebacic acid, phtalic acid, phtalic acid anhydride, tetrachlorophtalic acid anhydride, endomethylene tetrahydrophthalic acid anhydride, glutaric acid anhydride, maleic acid, maleic acid anhydride, fumaric acid, dimeric and trimeric fatty acids such as oleic acid, optionally in admixture with monomeric fatty acids, terephthalic acid dimethyl ester and terephtalic acid bisglycol ester. Examples of suitable polyhydric alcohols are ethylene glycol, 1,2- and 1,3-propylene glycol, 1,4- and 2,3-butylene glycol, 1,6-hexane diol, 1,8-octane diol, neopentyl glycol, cyclohexane dimethanol (1,4-bis-hydroxy methyl cyclohexane), 2-methyl-1,3-propane diol, also diethylene glycol, triethylene glycol, tetraethylene glycol, polyethylene glycols, dipropylene glycol, polypropylene glycols, dibutylene glycol and polybutylene glycols. Polyesters of lactones, for example, epsoloncaprolactone or hydroxy carboxylic acids, for example, w-hydroxycaproic acid, may also be used.

The polyethers containing at least 2, generally 2 to 8, but preferably 2 to 3 hydroxyl groups used in accordance with the invention are also known per se and are obtained, for example, by polymerizing epoxides, such as ethylene oxide, propylene oxide, butylene oxide, tetrahydrofuran, styrene oxide or epichlorohydrin on their own, for example, in the presence of $BF_3$, or by adding these epoxides, optionally in admixture or in succession, to starter components containing reactive hydrogen atoms, such as water, alcohols, or amines, for example, ethylene glycol, 1,3- or 1,2-propylene glycol, 4,4'-dihydroxy diphenyl propane, aniline, ammonia, ethanolamine or ethylene diamine. The most preferred polyether diol are poly(tetramethylene ether) glycols.

The use of trihydric and tetrahydric alcohols should be employed when cross-linking is desired for rendering the polyurethane thermosetting.

The polyurethane prepolymers are prepared by conventional means well known to the skilled artisan. The NCO/OH ratio is generally greater than 1 to give free NCO groups in the prepolymer. Generally this procedure involves heating while mixing the glycols to their melting point and then adding the polyisocyanate during mixing to enable formation of the prepolymer and stopping the reaction before the polymerization reaction is complete. Once prepared, the prepolymer is dispersed or dissolved in a solvent at the appropriate concentration of about 5% to about 40% and the polyurethane substrate is contacted to form a layer of prepolymer upon the polymer substrate. Once contacting is complete, the structure is placed in a nitrogen environment to remove the solvent and is then ready for reaction with the polymeric amine. The solvents may be selected from a wide variety of materials that are capable of dispersing the prepolymer which are volatilizable at temperatures below the melting point of the polymer substrate and prepolymer. Exemplary solvents include ethyl acetate, acetonitrite, methylene chloride, tetrahydrofuran, and the like.

The polymeric amine used in the invention may be selected from the group consisting of a polyvinyl amine, a polyalkylenimine having 2 to 4 carbon atoms per amine unit and mixtures thereof. Although the polyalkylenimine polymers are branched, the amine unit may be shown by the formula.

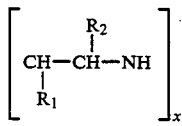

wherein $R_1$ is hydrogen, a methyl or ethyl group or larger with an attached amine and $R_2$ is hydrogen or another amino alkylene unit according to the formula. Exemplary materials include polyethylenimine and polypropylenimine. Polymers with a mixture of amine units are also able to be used such as polymers prepared by the polymerization of mixtures of ethylenimine and propylenimine. Polybutylenimine is also useable but not preferred. The average molecular weight of the polyalkylenimine is normally preferably 11,000 to 100,000 and represents multiples of x as shown.

The polymeric amine used in this invention must be covalently bound to the polymeric support. This may be conveniently done by coupling the polymeric amine directly to the polymer support or by coupling to a chemical arm or bonding layer previously coupled to the support. A preferred embodiment of the invention involves chemical reaction of the polymeric amine with activated amine groups via condensation interchange on the substrate or chemical reaction with free NCO units present on a prepolymer layered onto the support surface.

Reaction of the polymeric amine with the polymer substrate, either through condensation interchange or through a chemical arm or prepolymer layer is performed by dissolving the polymeric amine in water and contacting the activated sites to be bound for about 1 minute to 2 hours at 20° C. to about 50° C. The length of time needed to perform the bonding step as well as temperature of the solution may vary depending on such factors as the particular polymeric amine being used and concentration of the amine solution. It has been found acceptable to employ polymeric amine solutions containing from about 1% to abut 50% and preferably about 10% to about 20% by weight polymeric amine in the solution. Evaporating the water and postcuring the system for periods up to several days at 20° C. to about 50° C. may increase the covalent bonding.

In order to maximize the covalent bonding of the polymeric amine to the activated amino groups, the pH of the solution is maintained above 5.0, preferably from about 5.0 to about 12.0 and most preferably from about 7.0 to about 9.0.

Once the polymeric amine has been covalently coupled to the polymer support, the polymeric amine is washed essentially free of unbound polymeric amine. Washing may be performed with water or supplemented with a dilute and/or base wash.

Once washing is complete, the polymeric amine is reacted with an activated antithrombogenic agent to covalently bond the antithrombogenic agent to the polymeric amine. Activation of the antithrombogenic agent may be performed in various ways, such as chemical modification of the antithrombogenic agent with oxidizing or reducing agents. A particularly preferred way of activating the antithrombogenic agent is to couple the agent with a reactive chemical moiety that will enable covalent bonding of the agent to the polymeric amine. Exemplary agents that can be used as the activating agent may be selected from the group consisting of N-ethyl-5-phenylisoxazolium-3'-sulfonate, 1-ethyl-3-(3-dimethylaminopropyl) carbodiimide hydrochloride and 1-cyclohexyl-3-(2-morpholinoethyl) carbodiimide. The mere use of ionic salts of the antithrombogenic agent is not effective and merely results in the formation of leachable ionic bonds.

The antithrombogenic covalent bonding reaction, when using the preferred activating agents may vary from about 5 to 35 hours or more depending on such factors as the particular agent used, concentration of agent employed and degree of coupling achieved. Generally, the antithrombogenic agent solution concentration is from about 0.1 to about 30% by weight but may vary up to the solubility limit of the particular agent. The reaction is preferably performed at temperatures between 4° C. and 23° C. but may be performed at higher temperatures up to the deactivation temperature of the antithrombogenic agent.

The amount of activating agent employed will vary with the particular antithrombogenic agent and must be employed in the ratio of at least 1 molecule of activating agent to each molecule of antithrombogenic agent. When employing antithrombogenic agents that are polymeric in character, such as heparin which have repeating tetrasaccharide units, the equivalent ratio of the heparin to the activating agent may be 6–24 to one wherein the heparin equivalent weight is calculated on the basis of a tetrasaccharide moiety, namely 4 repeating saccharide molecules representing one unit.

Upon completion of the antithrombogenic coupling reaction, the surface may be washed with water to remove loosely bound or unreacted antithrombogenic agent. Washing may be optionally performed with an isotonic solution.

A procedure for preparing a preferred material according to the invention may be depicted from the following equation:

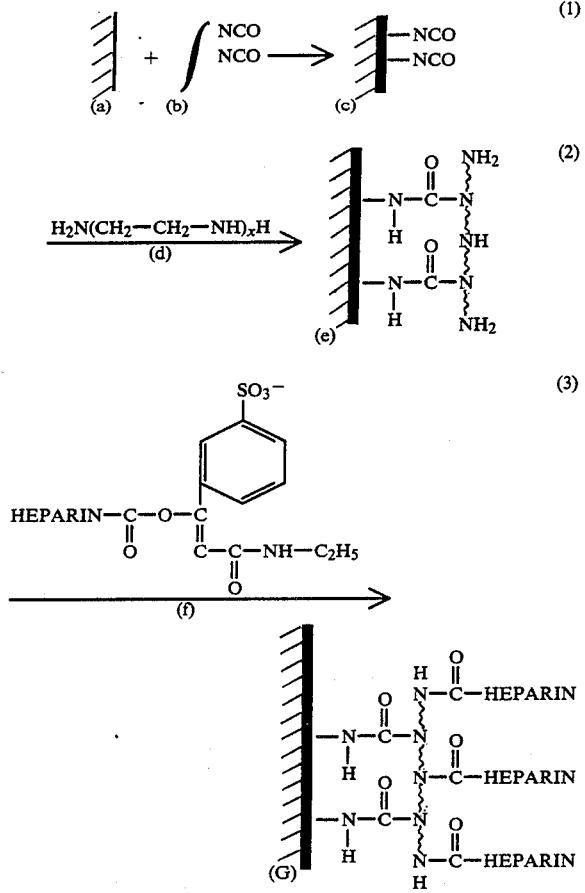

In the reaction equation scheme depicted, the polymeric support (a) is contacted with a polyurethane prepolymer (b) to prepare a solid support having free NCO units (c). The free NCO units are then reacted with a polyalkylenimine (d) to form a backbone support structure for coupling with the antithrombogenic agent (e). In the final step, heparin coupled to N-ethyl-5-phenylisoxazolium-3'-sulfonate (f) is reacted with the support to form a structure wherein heparin is covalently coupled to the polymeric support (g). The resulting covalently bonded heparin would demonstrate high antithrombogenic efficacy as well as permanency and nonleachability.

While the present invention has been described in terms of using polyurethane polymers as the support surface, it should be recognized that other solid support materials having active hydrogen groups or groups that can be aminolyzed by the polymeric amine are contemplated for use herein. Exemplary materials include polyamides, polyesters, and polyvinyl chlorides.

The invention will be further illustrated by the following non-limiting examples. All parts and percentages given throughout the Specification are by weight unless otherwise indicated.

EXAMPLE 1

Inventive Run 1

This example demonstrates the preparation and stability of structures of the invention using heparin as the antithrombogenic agent.

Samples of polyurethane tubing were dipped into a 40% solution of an NCO terminated prepolymer in ethylacetate having a 9.5% free NCO concentration. The NCO terminated prepolymer had the following formulation:

| Reactants | Equivalents | % Free NCO |
|---|---|---|
| Trimethylolpropane | 1 | 9.5 |
| Long chain polytetramethylene ether (650 average M.W.) | 1 | |
| Hydrogenated 4,4'-diphenyl methane diisocyanate | 4.0 | |
| Dibutyl tin dilaurate | (0.015%) | |

The NCO coated tubing was placed in a 25° C. enclosed environment for 30 minutes to flash the solvent. During the flash-off period, the atmosphere was continuously flushed with nitrogen. After 30 minutes, the tubing was transferred to a 20% solution of polyethylenimine at 50° C. After five minutes the tubing was removed and placed in a continuous flow water rinse for up to 48 hours to remove any non-covalently bound polyethylenimine. After the rinse period, the samples were then placed in a 0.25% solution of radio labeled heparin complexed with N-ethyl-5-phenylisoxazolium-3'-sulfonate for 16 hours at ambient conditions. Following the heparin reaction, the samples were exposed to a dynamic water rinse for varied times. The rinse is designed to remove any unreacted reagents. A known area of tubing was then dissolved in a solvent, placed in a scintillation counter and scintillation counting performed. It was shown that about 31 ug/cm$^2$ was bound to the polymer surface. The results are summarized in Table I and demonstrate that the heparin was covalently bonded to the support and was essentially non-leachable after successive washes.

TABLE I

| Heparin Bound (ug/cm$^2$) Rinse time (hr) | | | |
|---|---|---|---|
| 1 | 4 | 24 | 48 |
| 37.1 ± 2.0 | 33.3 ± 8.8 | 33.7 ± 2.7 | 31.1 ± 4.3 |

EXAMPLE II

Inventive Run 2 and Comparative Runs A and B

This example compares the partial thromboplastin time of structures made according to the invention compared to several non-inventive systems.

Round bottom shaped thimbles were made from the polyurethane of Example I by casting the polyurethane on the outside of a glass test tube. After the thimbles were stripped off and cut to size, they were treated as in Example I with a prepolymer having the formulation:

| Reagents | Equivalents | % Free NCO |
|---|---|---|
| Long chain polytetramethylene ether (650 average M.W.) | 1 | 6.6 |
| Hydrogenated 4,4'-diphenyl | 1.9 | |

| Reagents | Equivalents | % Free NCO |
|---|---|---|
| methane diisocyanate | | |
| Dibutyl tin dilaurate | (0.015%) | |

The samples were then subjected to exhaustive washing procedures to insure removal of any unreacted reagents. The samples were exposed to 144 hours of dynamic water rinse, followed by 144 hours in 0.855 sodium chloride, and finally to 72 hours in 3M sodium chloride. After a sample was removed from the 3M NaCl solution, it was rinsed with distilled water and dried in a desiccator before testing. Partial thromboplastin times (PTT) were determined for each thimble by the following procedure:

(a) The thimble was placed in a heating block well in a water bath at 37° C.
(b) 0.1 ml. fresh, citrated, platelet-poor plasma and 0.1 ml. partial thromboplastin reagent were pipetted into a thimble and incubated for five minutes.
(c) 0.1 ml. of 0.02 M $CaCl_2$ was added and a stop watch was started simultaneously.
(d) A nichrome loop was passed through the plasma mixture at a rate of two sweeps per second until the first strands of fibrin are detected.

Samples which were prepared in a similar manner were also tested by a modified PTT method, wherein step (b) of the previous procedure, "5 minutes" was changed to 30 minutes. The test demonstrates the need for truly covalent bonded systems to be incubated to allow the surface bound heparin to interact to produce an anticoagulant effect. The results are set forth in Table II.

TABLE II

| Sample | PTT (seconds) | 30 Min. Incubation PTT (seconds) |
|---|---|---|
| Glass (untreated) | 60 | 59 |
| Polyurethane (untreated) | 171 | 266 |
| Antithrombotic Polyurethane Polymer | 178 | 498 |

There is a clear improvement in the PTT time for the inventive structure over the glass and untreated polyurethane structures. This demonstrates antithrombogenic efficacy. The observed effect was not due to leached anticoagulant, but to a permanently bonded system. This is evidenced in three ways. First upon completion of the PTT testing, the plasma was removed from the thimble and analyzed by scintillation counting techniques showed no detectable radio labeled heparin for the inventive structure. This data shows that leached heparin was not responsible for the anticoagulant effect. Secondly, the PTT column of data in Table II shows the results of a normal (5 minute incubation) PTT test. There is no detectable anticoagulant effect. This demonstrates the system is not leachable but rather covalently bound. As such, the system requires incubation to show anticoagulant effect. Finally, the PTT test showed an extension of clotting time over the controlled materials as seen in the 30 minute incubation results of Table II showing an anticoagulant effect.

A slight extension of PTT was observed in the untreated polyurethane after a 30 minute incubation. Although not wanting to be held to a particular theory, this result may be due to passivation via adsorption of such plasma proteins as albumin.

EXAMPLE III

Inventive Run 3 and Comparative Run C

This example compares the use of various amines to couple the antithrombogenic agent to the support.

Tubes identical to those used in Example I were coated with the NCO terminated prepolymer of Example I. A portion of the samples were treated exactly as in Example I. A second portion of the tubes were treated in the same manner except a 20% aqueous solution of 1,6-hexanediamine was used in place of 20% polyalkylenimine. The results are shown in Table III.

TABLE III

| | Treatment | Amount Heparin Bound (ug/cm$^2$) |
|---|---|---|
| Polyurethane | Polyalkylenimine | 25–30 |
| Polyurethane | 1,6-hexanediamine | 1 |

The amount of heparin permanently bound to the inventive tube was significantly greater than that achieved in the comparative technique.

EXAMPLE IV

Inventive Run 4

This example demonstrates the preparation of structures according to the invention using an acid etch of the polymeric surface to provide reactive amine and hydroxyl groups.

Samples of polyurethane tubing were exposed to 3N hydrochloric acid for a period of 18 hours. This treatment was then followed by 3 hours in boiling water. The tubing samples were subsequently dried and reacted for 24 hours with hydrogenated 4-4'-diphenyl methane diisocyanate or the hydrogenated form of the latter to which 0.15% dibutyl tin dilaurate has been added.

The resulting NCO group is then converted to amine by reaction with a 25% solution of polyethylenimine for a period of 4 hours. The resulting structure was washed extensively in distilled water. Finally, the structure was exposed to a solution of activated heparin, where the heparin concentration of 0.25% in water having 20% of the —COOH groups of the heparin activated via N-ethyl-5-phenylisoxazolium-3'-sulfonate. The modified polyurethane surface was then washed in 3M NaCl for a period of 24 hours to remove any loosely or non-covalently bound heparin. The resulting heparin products were nonleachable when washed.

The invention being thus described, it will be obvious that the same may be varied in many ways. Such variations are not to be regarded as a departure from the spirit of scope of the invention and all such modifications are intended to be included within the scope of the claims.

What is claimed is:

1. An antithrombogenic polyurethane polymer which comprises:
   (a) a polyurethane substrate;
   (b) a polymeric amine selected from the group of a polyvinyl amine, a polyalkylenimine having 2 to 4 carbon atoms per amine unit and mixtures thereof covalently bonded to said polyurethane substrate; and
   (c) an antithrombogenic agent covalently bonded to said polymeric amine.

2. The antithrombogenic polyurethane polymer of claim 1 wherein the antithrombogenic material is selected from the group consisting of heparin, prostaglandins, urokinase, streptokinase, sulfated polysaccharide, albumin and mixtures thereof.

3. The antithrombogenic polyurethane polymer of claim 1 wherein the polyurethane polymer is selected from thermosetting polyurethane polymers and thermoplastic polyurethane polymers.

4. The antithrombogenic polyurethane polymer of claim 1 wherein the polyalkylenimine is selected from the group consisting of polyethylenimine, polypropylenimine, polybutylenimine and mixtures thereof.

5. The antithrombogenic polyurethane polymer of claim 1 wherein the polymeric amine has an average molecular weight of at least about 11,000.

6. The antithrombogenic polyurethane polymer of claim 1 wherein the polymeric amine is covalently bonded to the polyurethane substrate through a polyisocyanate prepolymer.

7. The antithrombogenic polyurethane polymer of claim 6 wherein the polyisocyanate prepolymer contains 2 to 30% free NCO units.

8. The antithrombogenic polyurethane polymer of claim 1 wherein the polymeric amine is covalently bonded to the polyurethane substrate through the activation of polyurethane surface functional amine groups.

9. The antithrombogenic polyurethane polymer of claim 1 wherein the antithrombogenic agent is activated with an activating agent to enable covalent coupling to the polymeric amine.

10. The antithrombogenic polyurethane polymer of claim 9 wherein the activating agent is selected from the group consisting of N-ethyl-5-phenylisoxazolium-3'-sulfonate, 1-ethyl-3-(3-dimethylaminopropyl) carbodiimide hydrochloride) and 1-cyclohexyl-3-(2-morpholinoethyl) carbodiimide.

11. A process for imparting antithrombogenic activity to polyurethane polymer materials, which comprises:
(a) treating the surface of the polyurethane polymer material with a solution of a polymeric amine selected from the group consisting of a polyvinyl amine, a polyalkylenimine having 2 to 4 carbon atoms per amine unit and mixtures thereof so that the polymeric amine becomes covalently bonded to said polyurethane substrate, wherein the pH of the polymeric amine solution is at least about 5.0.
(b) washing said surface essentially free of any non-covalently bonded polymeric amine; and
(c) treat the surface with an activated antithrombogenic agent to covalently bond the antithrombogenic agent to the polymeric amine.

12. The process of claim 11 wherein the antithrombogenic material is selected from the group consisting of heparin, prostaglandins, urokinase, streptokinase, sulfated polysaccharide, albumin and mixtures thereof.

13. The process of claim 11 wherein the polyurethane polymer is selected from thermosetting polyurethane polymers and thermoplastic polyurethane polymers.

14. The process of claim 11 wherein the polyalkylenimine is selected from the group consisting of polyethylenimine, polypropylenimine, polybutylenimine and mixtures thereof.

15. The process of claim 11 wherein the polymeric amine has an average molecular weight of at least about 11,000.

16. The process of claim 11 wherein the polymeric amine is covalently bonded to the polyurethane substrate through a polyisocyanate prepolymer.

17. The process of claim 16 wherein the polyisocyanate prepolymer contains 2 to 30% free NCO units.

18. The process of claim 11 wherein the polymeric amine is covalently bonded to the polyurethane substrate through the activation of polyurethane surface functional amine groups.

19. The process of claim 18 wherein activation of the polyurethane substrate is achieved by testing the polyurethane surface with concentrated hydrochloric acid.

20. The process in claim 11 wherein the pH of the polymeric amine solution is from about 5.0 to about 12.0.

21. The process of claim 20 wherein the pH of the polymeric amine solution is from about 7.0 to about 9.0.

22. The process of claim 11 wherein the antithrombogenic agent is activated with an activating agent to enable covalent coupling to the polyamine.

23. The process of claim 22 wherein the activating agent is selected from the group consisting of N-ethyl-5-phenylisoxazolium-3'-sulfonate, 1-ethyl-3-(3-dimethylaminopropyl) carbodiimide hydrochloride) and 1-cyclohexyl-3-(2-morpholinoethyl) carbodiimide.

* * * * *